United States Patent [19]

Yang et al.

[11] Patent Number: 4,851,683
[45] Date of Patent: Jul. 25, 1989

[54] ELEMENT SPECIFIC RADIO FREQUENCY DISCHARGE HELIUM PLASMA DETECTOR FOR CHROMATOGRAPHY

[75] Inventors: Frank J. Yang, Salt Lake City; Paul B. Farnsworth; Karin E. Markides, both of Provo; Milton L. Lee, Pleasant Grove; Ronald J. Skelton Jr., Orem, all of Utah

[73] Assignee: Brigham Young University, Provo, Utah

[21] Appl. No.: 24,095

[22] Filed: Mar. 9, 1987

[51] Int. Cl.⁴ .......................................... G01N 21/73
[52] U.S. Cl. .................................. 250/339; 250/340; 356/316
[58] Field of Search ................. 250/339, 340; 356/72, 356/316; 436/35, 155; 73/23.1

[56] References Cited

U.S. PATENT DOCUMENTS

| 4,309,187 | 1/1982 | Dodge, III et al. | 436/172 |
| 4,470,699 | 9/1984 | Gay | 356/316 |
| 4,509,855 | 4/1985 | Gay | 356/316 |
| 4,532,219 | 7/1985 | Hagen et al. | 356/316 |
| 4,586,368 | 5/1986 | Rice et al. | 73/23.1 |

OTHER PUBLICATIONS

Serravallo et al., "Effect of Doping Gases on Microwave-Induced Emissive Spect. Detectors for Gas Chroma." Anal. Chem. vol. 47, No. 13, (1975) p. 2141.
Durrant et al., "Techn. for G. C. and Optical Emm. Anal." Lab. Equip. Digest. vol. 11, No. 4, pp. 156-160, 4/1973.
Schwarz, "Quant. Anay. for $H_2O$ with MPD" Analytical Chem. vol. 50, No. 7, (Jun.-78).
Maybad et al. "Effect of $O_2$ on . . . Rad. Polymer in M.P.D." Polymer Letters Ed (USA), No. 11, vol. 15, pp. 693 (Nov.-77).
Lichte et al., "Analysis of Sol. Samp. by MPD" Analytical Chem. vol. 45, No. 2, (Feb.-73) p. 399.

Primary Examiner—Janice A. Howell
Assistant Examiner—Richard Hanig
Attorney, Agent, or Firm—Pennie & Edmonds

[57] ABSTRACT

A method and apparatus for element specific detection in chromatogragphic eluents. The apparatus is comprised of a radio frequency discharge between electrodes in helium, and utilizes a low-resolution plasma emission spectrometer to monitor selected spectral emissions produced when the helium discharge decomposes and excites the atomic constituents in chromatographic column effluents. The spectrometer is tuned to an atomic emission line in the near-infrared portion of the spectrum, and the emission intensity from the discharge region of a selected line is used to monitor the concentration of the element producing that line. Acceptable detector sensitivity is achieved by the use of a high-throughput optical system. Selectivity is achieved by a combination of correct line selection, plasma and carrier gas purification, and plasma gas doping.

93 Claims, 6 Drawing Sheets

| 0 | 4.5 | 9.5 | 14.5 | 19.5 | Time(min.) |
| 60 | 100 | 150 | 200 | 250 280 | Temp. °C |

FIG. 4B

ELEMENT SPECIFIC RADIO FREQUENCY DISCHARGE HELIUM PLASMA DETECTOR FOR CHROMATOGRAPHY

TECHNICAL FIELD OF THE INVENTION

The present invention relates to the use of spectral emission lines generated in a radio frequency helium discharge to achieve the element specific detection of compounds eluting from a chromatographic column.

DISCUSSION OF BACKGROUND AND PRIOR ART

Chromatography is a method of chemical analysis in which chemical components in a mixture are separated from each other before detection. The fundamental mechanism of separation is based on the relative distributions of the mixture components between a mobile phase and a stationary phase. The most popular form of chromatography is where the stationary phase is packed or coated inside a length of tubing, and the mobile phase flows through the tubing (or chromatographic column) by the application of pressure. The stationary phase can be an adsorbent or an immobilized polymeric material, while the mobile phase can be a gas, a liquid, or a super-critical fluid. The mobile phase carries the sample through the chromatigraphic column where the separation takes place and into a detector for detection of the separated components.

Detectors can be classified as either universal (nonselective) or selective. Universal detectors give a response for most chemicals, while selective detectors only respond to chemicals that contain certain elements or structural features. For example, the flame ionization detector is classified as a universal detector because it responds to any organic carboncontaining compound, and the flame photometric detector can be made specific for only sulfur-containing compounds by using an appropriate filter. Universal detectors are used when one is interested in the total composition of the sample mixture, while selective detectors are used to detect certain compounds or classes of compounds. Selective detectors are generally much more sensitive than universal detectors.

Among the most important selective detectors in chromatography are the element selective detectors. The most popular element-selective detectors are the electron capture detector (ECD), thermionic ionization detector (TID), the flame photometric detector (FPD), and the electrolytic conductivity detector (ELCD).

The ECD can achieve sub-picogram detection of halogen (F, Cl, Br) containing compounds, and has been widely used for the detection of pesticides, insecticides, drugs, and environmental pollutants. However, response factors and, hence, sensitivity vary considerably from compound to compound depending on the environment of the halogen atom in the molecule. The TID allows the most sensitive detection for compounds containing nitrogen and phosphorus, and has been used in the analysis of pesticides, petroleum, fossil fuels, food and flavors, clinical samples, drugs, and so on.

The FPD is mainly used for the selective detection of compounds containing sulfur or phosphorus, but can be used for the detection of halogens, nitrogen, and various metals. This detector is not as sensitive as the other element selective detectors, and the sensitivity can be further reduced by quenching of the signal if water or hydrocarbons are coeluted with the sample. Furthermore, the sulfer response of the FPD can vary from first-order to second-order depending on the heteroatom environment. The FPD has been widely used for the analysis of pollutants in air and water, pesticides, and fossil fuel-derived materials.

The ELCD offers picogram detection of nitrogen and sulfer, and sub-picogram chlorine detection limits. It is an important detection tool in the monitoring of environmental pollutants. However, due to the difficulties in its routine operation, column-to-detector interfacing, and loss of sensitivity due to the use of a solvent purge for minimizing connector, reactor, and scrubber dead volume, the ELCD is not as widely used as the other element-selective detectors.

In order to circumvent many of the problems associated with the element-selective detectors described above, and to produce a detector that can be tuned to any of a large number of elements instead of only a few, electrical discharge-type detectors have been investigated.

Several types of electrical discharges have been used for element selective detectors in chromatography, but all have suffered from deficiencies that have prevented their widespread use. Inductively coupled argon plasmas effectively decompose large amounts of organic materials, but provide poor excitation efficiency for the non-metallic elements that are of primary chromatographic interest. Inductively coupled plasmas have been operated with helium to give improved excitation of nonmetals, but the instrumentation is complex and expensive to operate. Microwave plasmas efficiently excite nonmetallic elements in low concentrations, but are intolerant of large sample loads and are often extinguished by the passage of the solvent during a chromatographic run. Direct current discharges have inhomogeneous excitation characteristics and tend to be unstable because of electrode heating and erosion. Nitrogen afterglow discharges produce complex background spectra and poor excitation of some nonmetals.

Gay, U.S. Pat. No. 4,509,855, discloses a direct current atmospheric pressure helium plasma emission spectrometer which contains two side-arms that receive effluents from a micro-column liquid chromatograph and a gas chromatograph. The plasma region is viewed through a light pipe positioned at an opening in the discharge tube. The opening penetrates directly into the plasma region leaving the plasma exposed to the atmosphere. The plasma is initiated when sufficient voltage is applied across the electrodes, and a large damping resistor is used to permit automatic reignition of the plasma after it is extinguished by the passage of a large quantity of sample.

Dodge, U.S. Pat. No. 4,309,187, discloses a method of analyzing for trace amounts of metals and other species capable of excitation by energy transfer from metastable excited nitrogen molecules. The metastable nitrogen is produced in a dielectric discharge and excites the species to be analyzed. The nitrogen source used for excitation is disclosed as air used at pressures below atmospheric pressure. The complex background spectrum produced by nitrogen discharges precludes their use as selective detectors for nonmetallic elements (Rice et al., Anal. Chem., 1981 53, 1519-1522).

Hagen, U.S. Pat. 4,532,219, discloses a microwave induced plasma used to create characteristic spectra from molecules and atoms immobilized in the discharge. Uniquely, Hagen used an apparatus that allows for the introduction of a non-volatile sample into the plasma cavity, and the plasma is transported to the sample following sample introduction.

Rice, U.S. Pat. No. 4,586,368, discloses a radio frequency electrodeless discharge. A grounding pin is used above the primary discharge electrode to produce an intense afterglow from which elemental emission is observed during a chromatographic run. In the visible and ultraviolet regions, where most emissions are monitored, interferences from molecular bands cause the selectivity of the detector to be poor.

BRIEF SUMMARY AND OBJECTS OF THE INVENTION

The invention is a chromatographic detector which consists of a radio frequency discharge generated in helium between a high potential electrode and a ground. The helium flow and discharge are contained in a chamber or "discharge tube" between the electrodes. A nonconducting cell body positions the electrodes and discharge tube, and prevents arcs from forming outside the discharge tube. A window through the nonconducting cell body allows emissions from the discharge region to be focused on the entrance aperture of a spectrometer using an optical device such as a lens or a mirror. The spectrometer is used to select characteristic emission from the element or elements to be monitored. The spectrometer may be a monochromator, a Fourier transform spectrometer, or a spectrograph. Light emerging from the spectrometer is detected by a photodetector with an extended red response. The signal from the photodetector is recorded as a function of time on a stripchart recorder or other suitable device.

It is, therefore, a primary object of this invention to provide improvements in the art of detecting specific elements in a sample excited in a plasma.

Another object of this invention is to provide improvement in the art of chromatographic analysis.

Another object of this invention is to provide a simplified apparatus for the element specific detection of components in chromatographic effluent streams.

Another object of this invention is to provide improvements in the method of detecting specific elements in a sample excited in a plasma.

Another object of this invention is to effectively reduce or eliminate background interferences common to infrared spectra.

Another object of this invention is to provide a means of creating a stable plasma which can accept effluents efficiently from gas, liquid, or supercritical fluid chromatographs.

These and other objects and features of the present invention will become more readily apparent as the apparatus and methods of practicing the invention are disclosed herein.

DETAILED DESCRIPTION OF THE INVENTION

The invention is best understood by reference to the following description and appended claims with reference to the drawings wherein the parts are designated with like numerals throughout.

The invention is a chromatographic detector which consists of an alternating current radio frequency discharge generated in helium between a high potential electrode and a ground. The helium flow and discharge are contained in a plasma containment chamber or "discharge tube" between the electrode and ground. A nonconducting cell body positions the electrodes and a discharge tube, and prevents arcs from leaving the discharge tube. A window through the nonconducting cell body allows emissions from the discharge region to be focused on the entrance aperture of a spectrometer using the optical device such as a lens or a mirror. The spectrometer is of specific design such that it has high optical throughput. The spectrometer is used to select characteristic emissions from the element or elements to be monitored. Light emerging from the exit slit is detected by a photodetector with an extended red response. The signal from the photodetector is recorded as a function of time on a stripchart recorder or other suitable device.

Sample effluent from the chromatograph is introduced directly from the chromatographic column into the interelectrode region of the discharge. A heated region between the oven and the detector base prevents condensation of the eluting compounds as they pass from the chromatographic oven to the detector. Helium plasma gas is added to the discharge tube at flow rates of between 1 and 200 mL/min. More particularly, in gas chromatography, helium plasma gas flow rates are commonly between 40 and 70 mL/min.

High-purity helium is used as the plasma gas in the detector. Helium is chosen over other noble gases because it gives the best excitation efficiency for non-metallic elements. It also provides better overall excitation efficiency than molecular gases, such as nitrogen, and has the added advantage of generating a simple background spectrum. The helium can be passed through oxygen traps and molecular sieve traps at liquid nitrogen temperatures in order to ensure its purity. After the traps, the helium can be split into two flows, one supplying the carrier flow for the chromatograph and the other supplying plasma gas for the detector. In order to reduce the possibility of leakage and atmospheric contamination, gas-tight seals (such as welded joints) are used in the helium supply lines in place of removable fittings.

Dopant gases, such as oxygen, can be added in low concentration to the helium in the discharge region. The dopant gas serves three purposes: it prevents the formation of carbon deposits on the walls of the discharge tube, it enhances atomic emission from the eluents by promoting fragmentation of the compounds entering the discharge, and it suppresses the formation of CN molecules, thus, reducing the intensity of band emission that they produce.

CN is a commonly observed impurity in the discharge that results from the reaction of atmospheric nitrogen and organic carbon. It is difficult to completely eliminate nitrogen contamination in the discharge region through mechanical means. Therefore, a dopant is added to selectively suppress the formation of CN. The dopant flow rate is precisely regulated in order to prevent flow-induced fluctuations in the discharge intensity. The flow rate of the dopant gas is selected such that the aforementioned effects are achieved without degrading the excitation performance of the helium plasma.

The present detector was designed to operate in the nearinfrared region of the electromagnetic spectrum in order to give it optimum sensitivity and selectivity while minimizing complexity and cost. The most intense atomic emission from many of the chromatographically interesting nonmetals is in the vacuum ultraviolet region of the spectrum. Detection in the vacuum ultraviolet region is complicated by the complexity of the required vacuum monochromators and by the presence of intense molecular emission from species produced during the elution of a chromatographic peak. Because of intense background emissions in the ultraviolet region of the spectrum, selectivity in the vacuum ultraviolet is poor. The problem of intense molecular background emission also exists in the ultraviolet and visible regions of the spectrum, making selectivity poor in these regions as well. The background emission in the near-infrared region of the spectrum is simple and relatively free from molecular bands. The notable exception is molecular emission from the CN molecule, which produces bands throughout the red and near-infrared spectral regions. The drawback to the near-infrared spectral region is the lack of sensitive detectors for wavelengths in these spectral regions.

Successful operation of the detector in the near-infrared spectral region is made possible by a combination of instrumental design features. The use of a dopant gas prevents the formation of CN molecules. In the absence of molecular background, it is possible to use a monochromator with low spectral resolution and correspondingly high optical throughput. Because of the simplicity of the background, a low resolution monochromator can be used without compromising selectivity. The high throughput of the optical system compensates for the poor response of commonly available photodetectors to near-infrared wavelengths and gives the instrument excellent overall sensitivity.

Because the monochromator is operated at first order wavelengths between 600 and 1000 nm, a short wavelength cutoff filter must be used to prevent higher order diffraction of shorter wavelengths from reaching the photodetector. This is particularly important when the photodetector is a photomultiplier tube. Because the gain of the photomultiplier tube is as much as four orders of magnitude higher for ultraviolet wavelengths than for near-infrared wavelengths, and because of the high intensity of emission from CO at short wavelengths produces during chromatographic peak elution, it is important that the cutoff characteristics of the order-sorting filter be as good as possible. Stray light is another potential source of background emission at the selected detection wavelengths. This can be minimized by the use of a different bandpass filter for each wavelength in place of the cutoff filter, or by the use of a double monochromator.

Figure 3A:
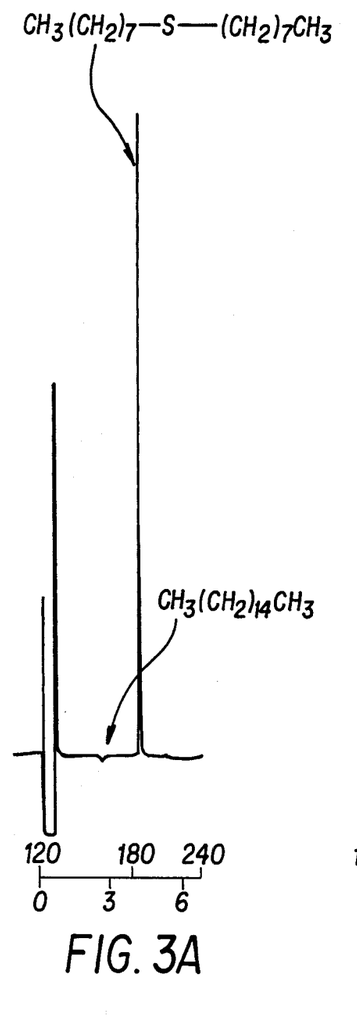
FIG. 3 is a comparison of chromatograms obtained using the disclosed invention of a mixture of hexadecane and octylsulfide with (3a) and without (3B) $O_2$ doping the plasma gas.
Figure 3B:
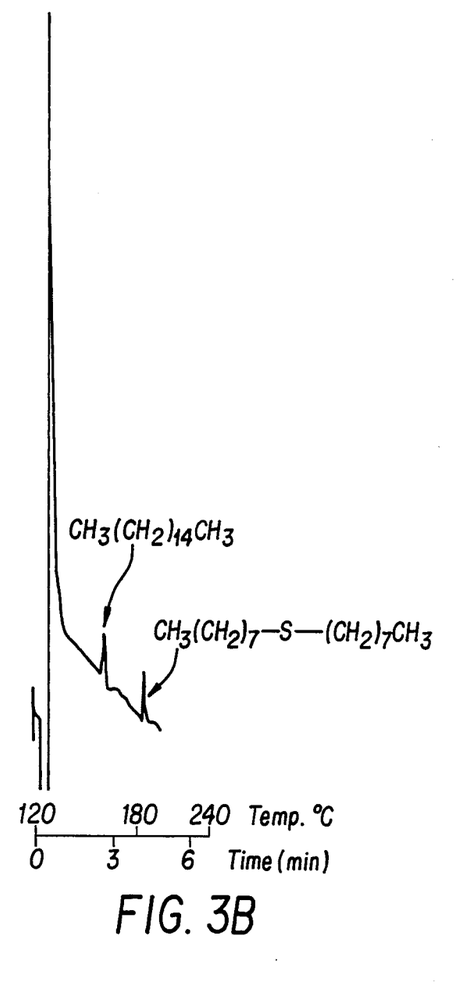

FIG. 3 shows chromatograms of a mixture of an aliphatic hydrocarbon (hexadecane) and an aliphatic sulfide (octylsulfide) obtained using the claimed invention. The detector was operated in the sulfer-selective mode at a wavelength of 921 nm. The mixture contained equal amounts of the two compounds. The chromatographic peaks represent 80 ng each. In the first chromatogram (3A), oxygen dopant was used at 0.03 mL/min flow rate. Excellent selectivity for sulfer was obtained, as can be seen by the absence of a chormatographic peak for hexadecane and the presence of a large peak for octylsulfide. In the second chromatogram (3B), no oxygen dopant was used, and poor sensitivity and no selectivity was obtained.

Figure 4A:
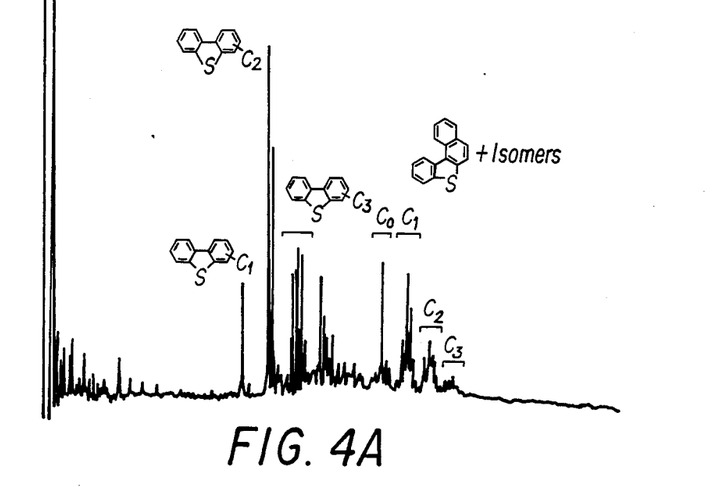
FIG. 4 is a comparison of chromatograms obtained using the disclosed invention of a sulfer-containing extract of a coal using selective detection for sulfer (4A) and selective detection for hydrogen (4B).
Figure 4B:
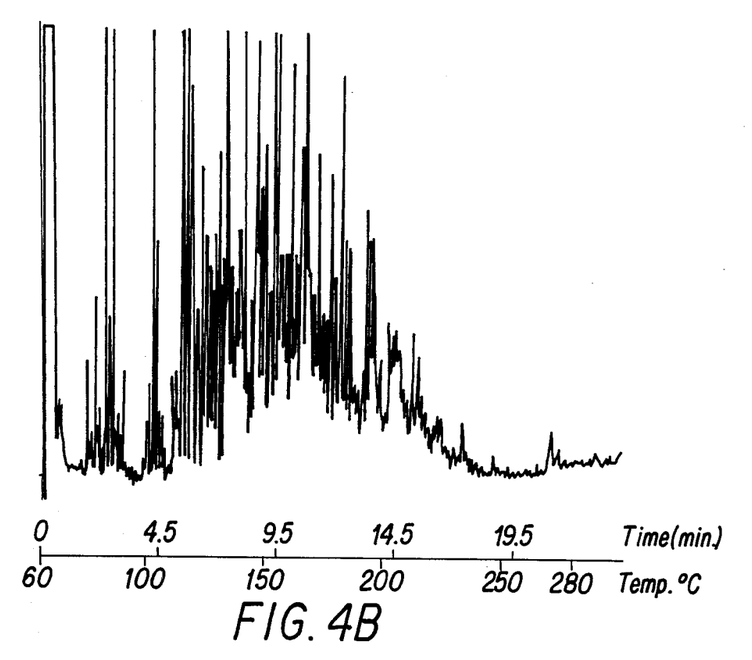

FIG. 4 shows chromatograms of an aromatic fraction of a coal extract at emission wavelengths of 921 nm (4A) and 656 nm (4B), selective for sulfur and hydrogen, respectively. In the hydrogen mode, the RPD is a sensitive universal detector for organic compounds, a property of the FID that has made it so popular. The selectivity of the RPD for sulfur has been determined to be greater than $10^3:1$. When the FPD was used to analyze this sample, significant quenching of the earlier eluting compounds was observed.

Figure 5A:
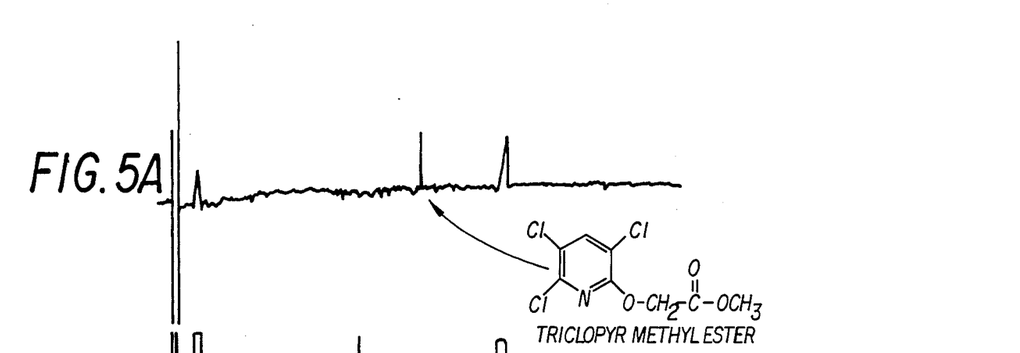
FIG. 5 is a comparison of chromatograms obtained using the disclosed invention of the methyl ester of the herbicide triclopyr in an extract from a Douglas fir, using selective detection for chlorine (5A) and selective detection for hydrogen (5B).
Figure 5B:
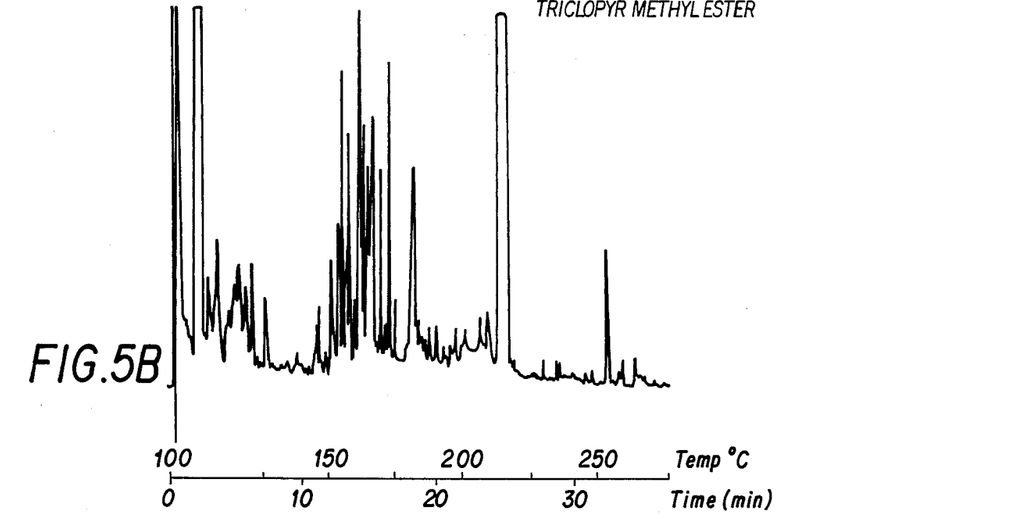

FIG. 5 demonstrates selectivity for chlorine using the RPD for the analysis of the methyl ester of the herbicide triclopyr in an extract from a Douglas fir. Detection in chromatogram 5A and 5B were accomplished in the chlorine and hydrogen modes, respectively. Again the complexity of the mixture can be seen using the detector in the hydrogen mode. Two extremely overloaded components in the mixture show up as broad peaks in the chlorine-selective mode. No dilution of the extract is needed, since these peaks are well-resolved from the compound of interest. Chlorine is detected at a wavelength that is free from interfering background (838 nm), and doping with an oxygen scavenger gas is not necessary. However, the use of oxygen to keep the discharge tube completely free from carbon deposits makes it advantageous to keep a constant low level of oxygen in the plasma. An example of the analysis of a trace level of Arochlor in a complex petroleum sample is demonstrated in Figure 6.

Figure 6A:
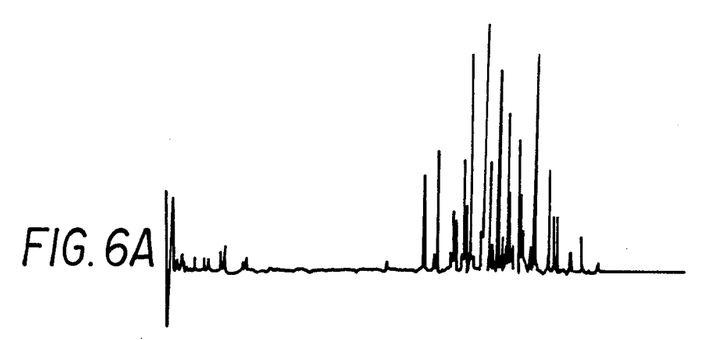
FIG. 6 shows chromatograms obtained using the invention of a complex petroleum sample including trace amounts of Arochlor. The analyses were performed in the chlorine (6A) and hydrogen (6B) modes.
Figure 6B:
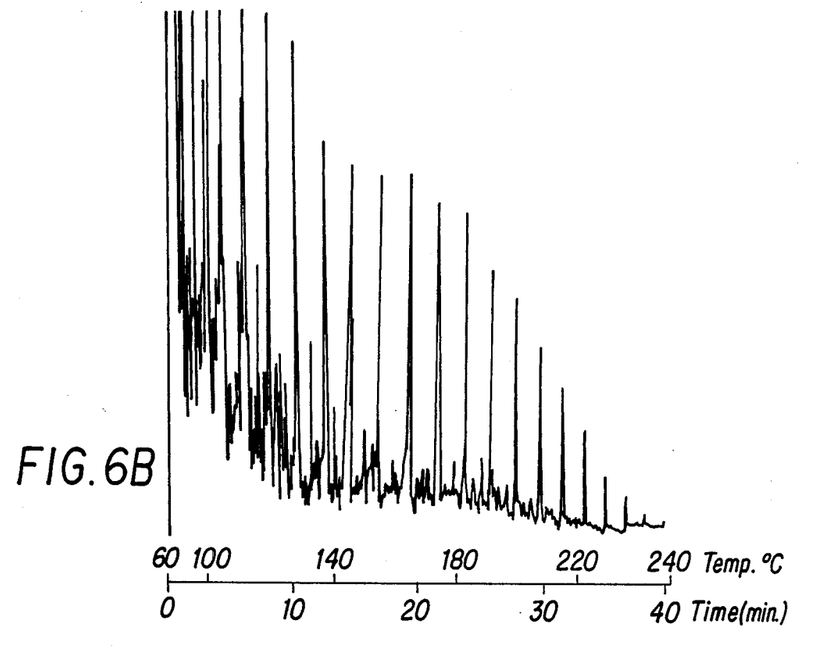

Detection in chromatograms 6A and 6B were accomplished in the chlorine and hydrogen modes, respectively.

The operational parameters and characteristics of the RPD for the elements H, S, Cl, Br, and I are listed in Table 1. The selectivity was calculated as grams of element to grams of carbon. The detector has excellent selectivity for sulfur and acceptable selectivity for the halogens, except for iodine. The RPD gives a linear response for these elements over three orders of magnitude, from the detection limit (see Table 1) except for chlorine for which a slight deviation could be detected at the upper concentration. While low sensitivities are commonly reported for detection in the near-infrared region, the design of this detector, however, utilizes the advantage of high throughput in the spectrometer while controlling the background spectrum by oxygen doping, thereby making it possible to achieve sensitivities in the 50 to 100 pg level.

Figure 1:
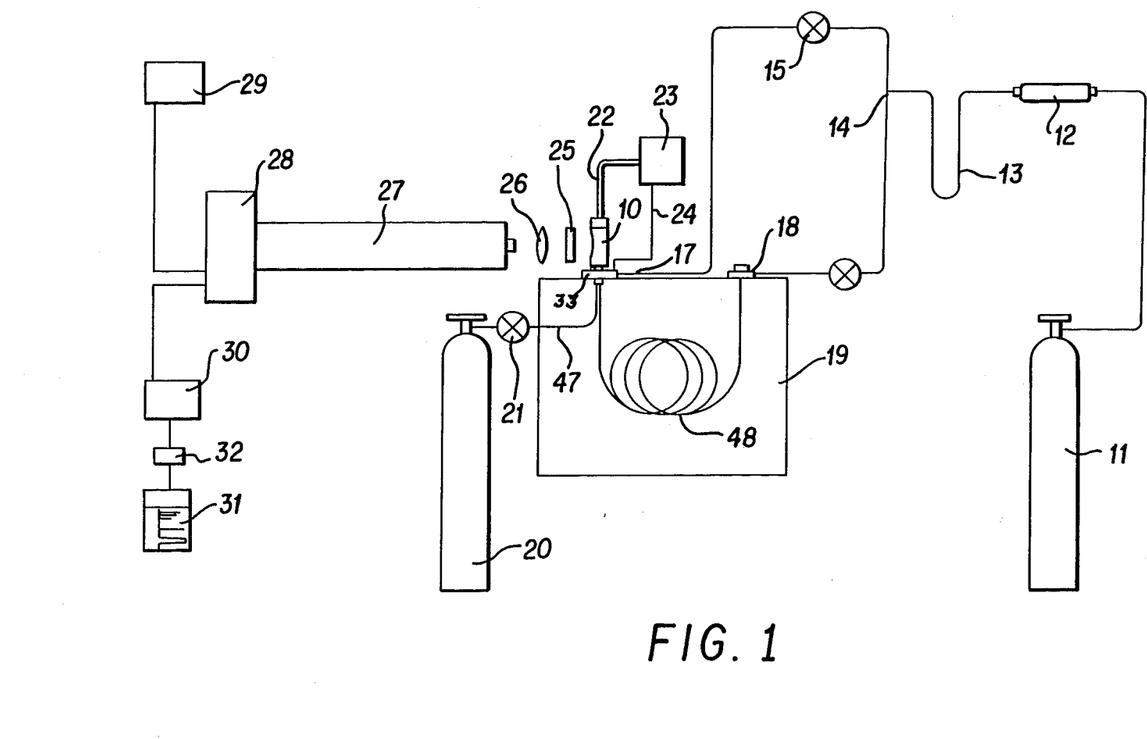
FIG. 1 is a schematic diagram of the detector being used in conjunction with a chromatograph.

Referring to FIG. 1, the high purity plasma gas 11 is preferably a 99.9999% pure helium which is obtainable from Scott Specialty Gases or other gas suppliers. The helium source must be as pure as possible because of the background interferences which result from impurities in the plasma gas. Should the purity of the helium be in question, additional purification steps can be taken, such as through the use of the oxygen trap 12. The oxygen trap is a commercially available trap, such as the "Oxytrap" manufactured by Alltech Associates. Use of the oxygen trap is optional for situations where the helium purity is in question.

TABLE 1

| | Operational Characteristics | | | |
|---|---|---|---|---|
| Element | Wavelength | Selectivity | Linearity | Sensitivity |
| Hydrogen | 656.3 nm | — | $10^3$ | 50 pg |
| Sulfur | 921.3, 922.8 923.7 nm | $>10^3$ | $10^3$ | 50 pg |
| Chlorine | 837.6 nm | $5 \times 10^2$ | $10^2$ | 75 pg |
| Bromine | 827.2 nm | $10^2$ | $10^3$ | 140 pg |
| Iodine | 905.8, 973.4 | 80 | $10^3$ | 100 pg |

In addition to the oxygen trap, a molecular sieve trap which is immersed in a liquid nitrogen bath is often required. The molecular sieve acts to remove residual water and other molecular contaminants which are present even in high purity helium sources. The molecular sieve consists of a mixture of 4 and 5 angstrom molecular sieve material which is commercially available from numerous chemical supply houses. Preferably, the sieve material is used as 8 to 12 mesh beads rather than as a powder.

Because the plasma gas purity is critical in this invention, each of the joints used in the plasma gas train must be atmospherically tight. In the preferred embodiment the train consists of a stainless steel tube and all joints between the two end points are sealed via welding techniques.

FIG. 1 illustrates a gas chromatographic configuration where the carrier gas and plasma gas are supplied from the same source via tee 14. However, in other gas chromatographic applications, as well as for both supercritical fluid chromatography and liquid chromatography, it is required to have separate plasma gas and carrier supplies. The carrier is used as the mobile phase in the chromatographic process which takes place in the chromatographic column 48. The column may be an open tubular or packed column. In the preferred embodiment, the column consists of a fused silica capillary column which is inserted directly into the discharge region of the radio frequency plasma source 10. The insertion directly into the source minimizes dead volume between the column and the detection device. However, the column effluent may be delivered at any point within the discharge tube. In order to preserve the gas-tight integrity of the system, the capillary column or connecting means is shown in the preferred embodiment as entering through the detector base via ferrule and fitting 46 (FIG. 2), which provides a gas-tight seal.

In order to eliminate certain interferences in the spectral emission, the effluent and plasma gas streams can be doped using various substances. For example, high purity oxygen can be used to scavenge carbon in the emission chamber. As the carbon is scavenged, the interfering CN emissions are reduced because the amount of carbon available to form the CN molecule is reduced. CN band emission is a significant spectral interference for many of the spectral lines that must be monitored in order to perform the desired analyses. Additionally, other dopant gases are used to control interferences. For example, $SF_6$ can be used to break up effluent molecules and scavenge free carbon, thus eliminating CN interferences and permitting oxygen to be detected. The detection of oxygen as an element in organic species is an extremely important analysis made possible by this invention. Other dopant gases include the freons, carbon tetrachloride, and other halogen-containing compounds. The dopant materials are introduced into the plasma discharge region at any point such that they will mix with the plasma gas. It has been found convenient to make the introduction via a capillary tube inlet which passes through the ferrule and fitting 46 up into the discharge tube past the plasma gas inlet, and terminates prior to introduction of the chromatographic effluent. The dopant tube inlet 47 is preferably constructed of fused silica capillary or other nonreactive material, and each joint along the pathway is atmospherically sealed.

Figure 2:
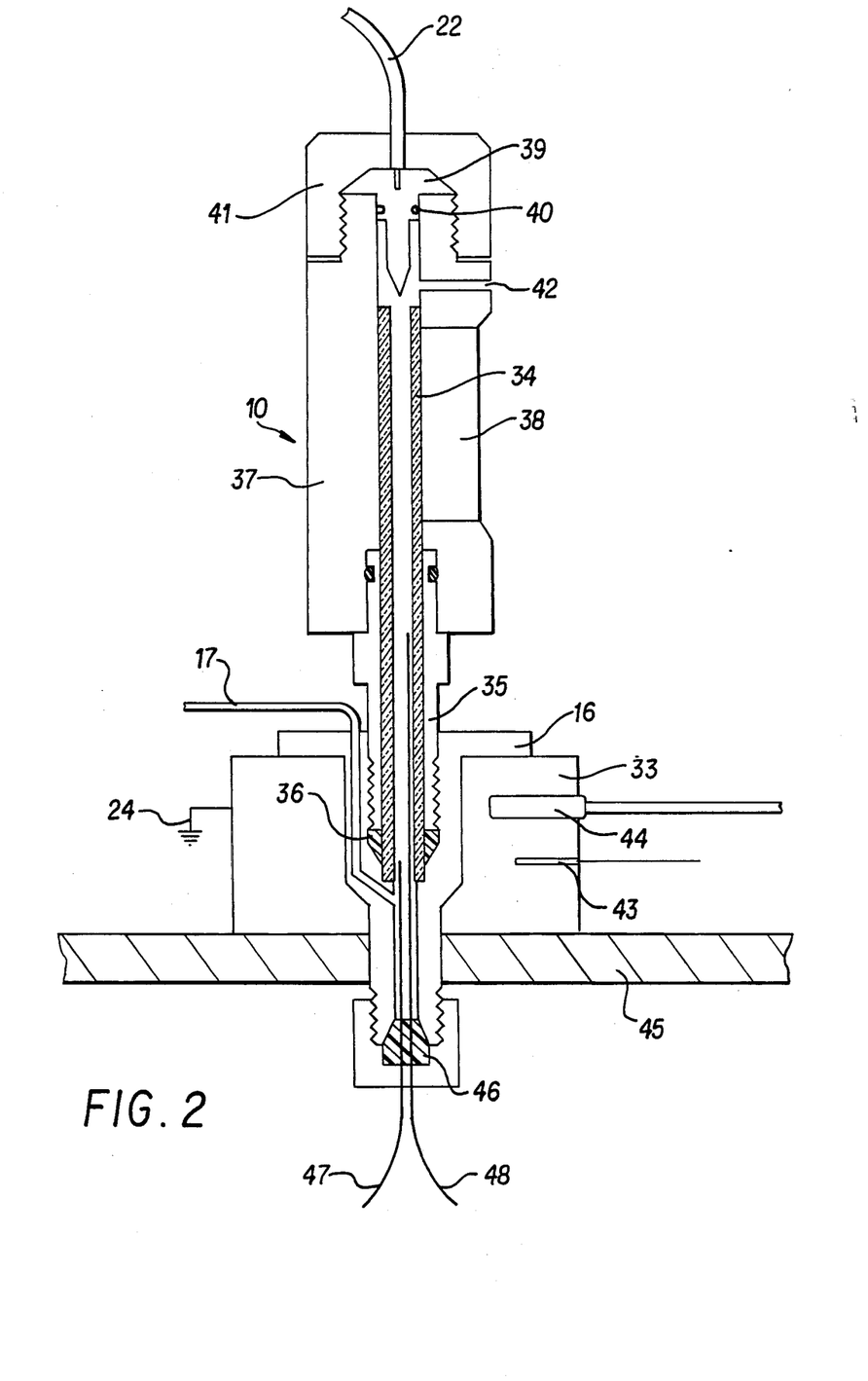
FIG. 2 is an enlarged view of a vertical cross section along the central axis of the detector apparatus of the disclosed invention.

In the preferred embodiment, the plasma gas is controlled by a needle valve 15 and introduced into the detector base 16 (FIG. 2). It passes through a passageway or channel through the base and is introduced into the discharge tube at its endpoint, prior to the introduction of the dopant tube or chromatographic effluent. The plasma gas then passes up the discharge tube around the dopant tube and chromatographic column or connecting tubing. The detector base 16 and the end of the chromatographic column or connecting tubing pass through heater block 33 in order to produce a controlled temperature environment through which the chromatographic effluents pass after leaving the chromatographic oven. It is important that the effluents be placed in an environment which ensures that they do not condense on the interior of the column or discharge tube. Heating prevents such condensation. The temperature of the heater block is monitored by a thermocouple 43 and is controlled via resistance heater module 44. The heater block is secured to the chromatographic oven wall 45 using screws, bolts, or other connectors. Heater block 33 is preferably made out of aluminum or other thermally conductive material. Detector base 16 is preferably constructed of stainless steel or other corrosion resistant metal and is heated through direct means or indirectly as a result of its contact with the heater block.

A connector 35 is used to secure the radio frequency plasma source 10 to the detector base 16 which is contiguous with the heater block 33. Preferably, connector 35 consists of a stainless steel nut which is threaded into the detector base and extends into the insulating cell body 37. Both the connector 35 and detector base 16 are hollowed to permit passage of the gases and columns feeding the discharge tube. The discharge tube 34 extends all of the way through the connector and into the detector base itself. A heating element can be extended into the insulating cell body in order to heat the discharge tube and pyrolyze materials that are deposited on the walls of the discharge tube. The extended element is preferably an extension of the detector base 16. Either this means of decarbonization and/or the addition of $O_2$ can be used to achieve decarbonization.

Discharge tube 34 is a nonreactive tube material such as fused silica, sapphire, or boron nitride. The wall of the tube must be able to pass the spectral emissions generated within it, such that they can be monitored. In the preferred embodiment, the outside diameter of the discharge tube is approximately 3 mm and the internal diameter is 1 mm, yielding a wall thickness of 1 mm of fused silica. However, the internal diameter of the discharge tube or plasma containment chamber can range between 0.05 mm and 10 mm.

In the event that the doping agents corrode the fused silica discharge tube, other tube materials must be used. The use of a boron nitride tube necessitates the insertion of a window into the wall of the discharge tube 34. A slight flow of helium across the window prevents corrosive species from reacting with the surface.

A helium plasma is generated in the discharge tube through the use of an alternating current radio frequency discharge between the high potential electrode 39 and the ground 24. The detector base 16 acts as the ground in the preferred embodiment. The high potential stainless steel electrode 39 receives current through the high voltage cable 22 from the power supply 23. In the event that halogen-containing or other corrosive dopants are used, the high potential electrode must be constructed of, or coated with, a more inert material such as gold or platinum. The electrode and ground are electrically insulated by the insulating cell body 37. The cell body is constructed of a ceramic or metallic oxide, such as aluminum oxide or other electrically insulating material, and encases the discharge region of the discharge tube 34. The cell body rests upon the connection 35 in order to provide a stable housing for the discharge tube. An O-ring or other seal may be used between the cell body and the connector 35 in order to ensure a stable connection. The high potential electrode is configured such that the discharge is directed through the discharge tube toward the ground 24.

The high potential electrode 39 is held in place and insulated from the surrounding environment by cap 41. The cap also acts, in conjunction with O-ring 40, to apply an atmospheric seal at the end of the discharge tube chamber. Gas outlet 42 permits the controlled escape of gases and effluents from the discharge tube into the atmosphere. Because of the restricted size of the outlet and the constant plasma gas flow maintained in the discharge tube, atmospheric contaminants do not traverse the outlet passageway and contaminate the plasma. An additional purge chamber may be constructed around the discharge tube outlet 42, or the discharge tube outlet may be extended, in order to further prevent back diffusion of atmospheric gases into the discharge tube.

A window 38 permits the monitoring of emissions through the wall of the discharge tube. If a transparent discharge tube, such as quartz or sapphire, is used, the window can be as simple as an opening through the insulating cell body, which exposes a portion of the discharge tube wall.

Referring again to FIG. 1, spectral emission viewed through the window is transmitted through filter 25 which is a wavelength cut-off filter or bandpass filter. A single filter or combination of filters can be used to eliminate undesirable background emission. Lens 26 is used to focus the light prior to entering the monochromator. Monochromator 27 is a monochromator of low to moderate resolution. The choice of spectral resolution depends on the nature of the background in the vicinity of the specific spectral line being monitored. In regions of low background, optimum sensitivity is obtained at low resolution without sacrificing selectivity. However, in the presence of high background, resolution must be increased to achieve the desired selectivity. The grating of the monochromator is blazed to permit operation in the near-infrared spectral region. A potential disadvantage of the use of the near-infrared region of the spectrum for the detection of atomic emission from the radio frequency plasma detector is the lack of photodetector sensitivity at near-infrared wavelengths. A high throughput optical system is required to offset this lack of sensitivity. Optical throughput is primarily a function of spectrometer design. The important design parameters in the spectrometer are: the ratio of the focal length of the spectrometer optics to their diameter (f number), the size of the entrance aperture to the spectrometer, and in the case of a grating monochromator, the blaze of the diffraction grating. For practical reasons, the spectrometers with the smallest f numbers are those with the shortest focal lengths and the poorest spectral resolution. An increase in entrance aperture size also results in a decrease in spectral resolution. The simplicity of the spectral background in the doped radio-frequency helium plasma allows the use of a low f number spectrometer with a large entrance aperture. spectral resolution can be sacrificed for sensitivity Acceptable selectivities and sensitivities are achieved despite the poor sensitivity of near-infrared photodetectors. Photomultiplier tube 28 is designed specifically for use in the near-infrared region of the spectrum. Signals from the photomultiplier tube 28 are collected by electrometer 30 which in turn passes the signal through a low-pass filter 32 in order to remove high frequency noise. The signal is then recorded on recording device 31 which is commonly a simple strip-chart recorder. Other recording devices such as electronic integrators and digital data loggers could be used.

Preferred Embodiment

Referring to FIG. 1, there is illustrated a chromatographic system incorporating the radio frequency plasma source 10. The chormatographic system consists of a source of high-purity plasma gas 11, which is preferably helium, connected to an oxygen trap 12 and a cryogenic molecular sieve 13. The helium then passes to a tee 14, which splits it into two streams. One stream passes through a metering valve 15 and into the plasma gas inlet 17 on the detector base 16. The second stream is connected to the carrier gas inlet 18 on the chromatograph 19. The chromatograph includes an injector, a temperature controllable oven, and a gas chromatographic column 48. The column is connected directly to the base of the radio frequency plasma source 10. A source of dopant gas 20 is also connected via dopant tube 47 to the plasma source 10 through a metering valve 21. The high voltage lead 22 from the radio frequency power supply 23 is connected to the high potential electrode at the top of the plasma source 10. The ground lead 24 from the power supply 23 is connected to the heater block 33 at the base of the plasma source 10. Light from the plasma source passes through a filter 25 and is collected by a lens 26. The light is focused on the entrance slit of a monochromator 27. The monochromator is tuned to a selected wavelength and the light intensity is quantified by a redsensitive photomultiplier tube 28. Power to the photomultiplier tube is supplied by a stable high-voltage power supply 29. The output of the photomultiplier tube is amplified by an electrometer 30, filtered by a low-pass filter 32, and recorded as a function of time by a recording device 31.

Referring now to FIG. 2, radio frequency emission source 10 consists of discharge tube 34 which is supported by a connector 35 that is threaded into the detector base 16. A gas-tight seal to the base is provided by ferrule 36. A plasma gas inlet 17 introduces plasma gas into the discharge tube via a passageway through the detector base. Contiguous with the connector 35 is an insulating cell body 37 which separates the high-potential and ground electrodes and forces the discharge to occur within the discharge tube 34. A viewing window 38 in the insulating cell body allows radiation to be monitored through the wall of the discharge tube. The high potential electrode 39 is inserted in the cell body. A seal 40 prevents the entry of atmospheric contamination through the top of the cell body. An alternating current discharge is maintained between the high-potential electrode 39 and the grounded detector base 16. An insulating cap 41 holds the high-potential electrode in place. A gas outlet 42 provides a channel for the controlled exit of plasma and carrier gases from the cell body. The detector base is connected to the chromatographic oven through a heater block 33 which prevents condensation of the chromatographic effluent as it passes from the oven to the detector. The temperature of the heater block is monitored through a thermocouple 43 and maintained by a resistance heater 44. An extension of the detector base 16 passes through the chromatographic oven wall 45. The chromatographic column 48 is sealed to the detector base by ferrule and fitting 46. Dopant gas is introduced into the discharge tube through dopant gas tube 47. The dopant gas tube is sealed to the base by ferrule and fitting 46.

While the invention has be described and illustrated with reference to specific embodiments, those trained in the art will recognize that modifications and alternations may be made without departing from the principles of the invention as described hereinabove and asset forth in the following claims.

Having thus described and illustrated the invention what is claimed is:

1. A detector for detector specific elements in the effluent stream of a chromatograph comprising:
    a plasma containment chamber having an inlet, an outlet, and a viewing means for exposing a portion of said plasma containment chamber to a monitoring means;
    sampling means for introducing a sample from the effluent stream of a chromatograph into said plasma containment chamber;
    plasma means for creating a plasma in said plasma containment chamber, said plasma exciting atomic and molecular components in said sample, thereby creating spectral emissions;
    monitoring means sensitive to red and infrared radiation for detecting said spectral emissions through said viewing means, said monitoring means comprising a spectrometer having high optical thoughput; and
    dopant means for introducing a dopant into said plasma in said plasma containment chamber in order to selectively reduce spectral interference from said plasma containment chamber, said dopant comprising a gas of a material for selective combination with molecular species which would otherwise produce interfering emissions in said plasma in the red and infrared regions of the electromagnetic spectrum.

2. The detector of claim wherein the same plasma containment chamber is a fused silica tube.

3. The detector of claim 2 wherein said tube has an i.d. of between 0.05 mm and 10 mm.

4. The detector of claim 2 wherein said tube is a portion of a chromatographic column.

5. The detector of claim 1 wherein the said plasma containment chamber is a sapphire tube.

6. The detector of claim 5 wherein the said tube has an i.d. of between 0.05 mm and 10 mm.

7. The detector of claim 1 wherein the said plasma containment chamber is a boron nitride tube.

8. The detector of claim 7 wherein said tube has an internal diameter of between 0.05 mm and 10 mm.

9. The detector of claim 1 wherein the said plasma containment chamber has a transparent portion which allows viewing of the said spectral emissions.

10. The detector of claim 1 wherein the said viewing means is an opening passing through any materials obscuring direct viewing of the said transparent portion of the said plasma containment chamber.

11. The detector of claim 1 wherein the said sampling means is a connection to the outlet end of a chromatographic column.

12. The detector of claim 1 wherein the sampling means is heated.

13. The detector of claim 12 wherein the sampling means is heated as a consequence of its being within, or a portion of, the detector base or the heating block, which base and heating block are heated in a controlled manner.

14. The detector of claim 1 wherein the sampling means is positioned such that the sample is introduced directly into the plasma of the electrical discharge region.

15. The detector of claim 1 wherein the said plasma means is an alternating current radio frequency electrical discharge.

16. The alternating current radio frequency electrical discharge of claim 15 wherein said discharge passes between a high potential electrode and a ground.

17. The detector of claim 1 wherein the said plasma is helium.

18. The detector of claim 1 wherein the said plasma means directs the electrical discharge through the plasma containment chamber, by having the discharge extend from a small surface area of the high potential electrode to the ground.

19. The detector of claim 1 wherein said plasma means is electrically insulated by an insulator which encases the plasma containment chamber and separates the high potential electrode and the ground.

20. The detector of claim 19 wherein the said insulator is any material having a high dielectric constant.

21. The detector of claim 19 wherein the said insulator is a ceramic.

22. The detector of claim 19 wherein the said insulator is a metallic oxide.

23. The detector of claim 1 wherein the said plasma means has an inlet to receive plasma gas into the plasma containment chamber.

24. The detector of claim 1 wherein the said monitoring means is a monochromator optimized for use in the near-infrared spectral region.

25. The detector of claim 1 wherein the said monitoring means is a Fourier transform spectrometer.

26. The detector of claim 1 wherein the said monitoring means is a spectrograph with a photodiode array in the focal plane.

27. The detector of claim 1 wherein said dopant is controllably introduced in the plasma gas prior to exposure to the said creation of spectral emissions.

28. The detector of claim 1 wherein the said dopant is $O_2$.

29. The detector of claim 1 wherein the said dopant is a halogen containing compound.

30. The detector of claim 29 wherein said compound is $SF_6$.

31. The detector of claim 1, wherein said monitoring means further comprises a filter adapted to pass red and infrared radiation and absorb shorter wavelength radiation.

32. An alternating current radio frequency plasma discharge apparatus for element specific detection in multi-element chromatographic eluents comprising:
   sample introduction means;
   plasma gas inlet means;
   a plasma containment chamber;
   discharge electrodes having means for directing an electrical discharge through the plasma containment chamber;
   means for the electrical isolation of the plasma containment chamber;
   viewing window means for exposing a portion of the discharge region in the plasma containment chamber;
   means for isolating the plasma containment chamber from atmospheric contamination;
   means for allowing the plasma containment chamber to be purged of atomized elements and other effluents;
   means for monitoring selected molecular emissions from said plasma in the red and infrared regions of the electromagnetic spectrum;
   means for introducing a constant supply of molecular species into the plasma for reaction with other molecular species which would otherwise produce undesirable emissions in the red and infrared in the plasma; and
   plasma containment chamber decarbonization means.

33. The apparatus of claim 32 wherein the sample introduction means is a connection to the outlet end of a chromatographic column.

34. The apparatus of claim 32 wherein the sample introduction means is heated.

35. The apparatus of claim 34 further comprising detector base means and means for heating said detector base means in a controlled manner, and wherein the sample introduction means is in thermally conducting relation with said detector base means.

36. The apparatus of claim 32 wherein the sample introduction means is positioned such that the sample is introduced directly into the plasma of the electrical discharge region.

37. The apparatus of claim 32 wherein the plasma containment chamber is a fused silica tube.

38. The apparatus of claim 37 wherein said tube has an i.d. of between 0.05 mm and 10 mm.

39. The apparatus of claim 37 wherein said tube is a portion of a chromatographic column.

40. The apparatus of claim 32 wherein the plasma containment chamber is a sapphire tube.

41. The apparatus of claim 40 wherein the said tube has an i.d. of between 0.05 mm and 10 mm.

42. The apparatus of claim 32 wherein the plasma containment chamber is a boron nitride tube.

43. The apparatus of claim 42 wherein said tube has an internal diameter of between 0.05 mm and 10 mm.

44. The apparatus of claim 32 wherein the means of directing the electrical discharge through the plasma containment chamber is achieved by having the discharge extend from a small surface area of the high potential electrode to the ground.

45. The apparatus of claim 44 wherein said ground is the base of the detector which is electrically grounded.

46. The apparatus of claim 32 wherein the means for the electrical isolation of the plasma containment chamber is an insulator which electrically isolates the plasma containment chamber, and separates the high potential electrode and the ground.

47. The detector of claim 46 wherein the said insulator is any material having a high dielectric constant.

48. The detector of claim 46 wherein the said insulator is a ceramic.

49. The detector of claim 46 wherein the said insulator is a metallic oxide.

50. The apparatus of claim 32 wherein said plasma gas inlet means is a tube which delivers plasma gas to the plasma containment chamber.

51. The apparatus of claim 32 wherein the viewing window is an opening passing through the insulator which exposes portion of the discharge region of the plasma containment chamber.

52. The apparatus of claim 32 wherein said monitoring means is a monochromator optimized for use in the near-infrared spectral region.

53. The monochromator of claim 32 wherein the monochromator has a small f number and large entrance slits.

54. The apparatus of claim 32 wherein said monitoring means is a Fourier transform spectrometer.

55. The apparatus of claim 32 wherein said monitoring means is spectrograph with a photodiode array in the focal plane.

56. The apparatus of claim 32 wherein the molecular species which is introduced to prevent undesirable emission in the plasma is $O_2$.

57. The apparatus of claim 32 wherein the molecular species which is introduced to prevent undesirable emission in the plasma is a halogen-containing compound.

58. The apparatus of claim 32 wherein the molecular species which is introduced to prevent undesirable emission in the plasma is $SF_6$.

59. The apparatus of claim 32 wherein the molecular species which is introduced to prevent undesirable emission in the plasma is a halogenated hydrocarbon.

60. The apparatus of claim 32 wherein the decarbonization means is means for controllably adding $O_2$ as a dopant to the plasma gas.

61. The apparatus of claim 32 wherein the decarbonization means is a heating means used to heat the plasma containment chamber is order to pyrolyze residues which form on the chamber walls.

62. The apparatus of claim 32 further comprising a filter disposed between said viewing window means and said means for monitoring, said filter being adapted to pass red and infrared radiation and absorb shorter wavelength radiation.

63. A method for detecting specific elements in an effluent stream of a chromatograph comprising:
   obtaining a plasma containment chamber having an inlet, an outlet, and a viewing means for exposing a portion of said plasma containment chamber to monitoring means;
   introducing a sample from the effluent stream of a chromatograph into said plasma containment chamber;

creating a plasma in said plasma containment chamber such that the plasma excites atomic and molecular components in said samples, thereby creating spectral emissions;

monitoring said spectral emissions through a viewing means using a monitoring means comprised of a monochromator sensitive to red and infrared radiation, and having a small f number and large entrance slits;

and introducing a dopant into said plasma in said plasma containment chamber for the selective reduction of spectral interferences from said plasma containment chamber, said dopant being comprised of a gaseous medium for the selective prevention of the formation of molecular species which would otherwise produced undesirable emission in said plasma in the red and infrared region of the electromagnetic spectrum.

64. The method as set forth in claim 63 wherein the step of obtaining said plasma containment chamber is accomplished by using a fused silica tube.

65. The method as forth in claim 64 wherein said tube has an i.d. of between 0.05 mm and 10 mm.

66. The method as set forth in claim 63 wherein the step of obtaining said plasma containment chamber is accomplished by using a portion of a chromatographic column.

67. The method as set forth in claim 63 wherein the step of obtaining said plasma containment chamber is accomplished by using a sapphire tube.

68. The method as set forth in claim 67 wherein said tube has an i.d. of between 0.05 mm and 10 mm.

69. The method as set forth in claim 63 wherein the step of obtaining said plasma containment chamber is accomplished by using a boron nitride tube.

70. The method as set forth in claim 69 wherein said tube has an internal diameter of between 0.05 mm and 10 mm.

71. The method as set forth in claim 63 wherein the step of obtaining said plasma containment chamber is accomplished by using a chamber which has a transparent portion allowing viewing of the said spectral emissions.

72. The method as set forth in claim 63 wherein the step of obtaining a viewing means includes creating an opening passing through any materials obstructing direct viewing of the said transparent portion of the said plasma containment chamber.

73. The method as set forth in claim 63 wherein introducing a sample is accomplished through a connection to the outlet end of a chromatograph column.

74. The method as set forth in claim 63 wherein the introduction of said sample into said plasma containment chamber utilizes a heated introduction means.

75. The method as set forth in claim 74 wherein the said heated sampling means is obtained as a consequence of passing the sample within the detector base or the heating block, which base and heating block are heated in a controlled manner.

76. The method as set forth in claim 63 wherein the introduction of a sample is accomplished by positioning the introduction means such that the said sample is introduced directly into the plasma of the electrical discharge region.

77. The method as set forth in claim 62 wherein the creation of the plasma is accomplished using an alternating current radio frequency electrical discharge.

78. The method as set forth in claim 77 wherein the said alternating current radio-frequency electrical discharge is achieved by passing a discharge between a high potential electrode and a ground.

79. The method as set forth in claim 63 wherein the said plasma is formed from a plasma which is helium.

80. The method as set forth in claim 63 wherein the said plasma is created using an electrical discharge which passes through the plasma containment chamber, said discharge extending from a small surface area of the high potential electrode to the ground.

81. The method as set forth in claim 63 wherein the said plasma containment chamber is electrically insulated using an insulator which encases the plasma containment chamber and separates the high potential electrode and the ground.

82. The method as set forth in claim 81 wherein the insulator is any material having a high dielectric constant.

83. The method as set forth in claim 81 wherein the said insulator is a ceramic.

84. The method as set forth in claim 81 wherein the said insulator is a metallic oxide.

85. The method as set forth in claim 63 wherein the said plasma containment chamber has an inlet to receive plasma gas into the said plasma containment chamber.

86. The method as set forth in claim 63 wherein the said monitoring is achieved using a monochromator optimized for use in the near-infrared spectra region.

87. The method as set forth in claim 63 wherein the said monitoring is achieved using a Fourier transform spectrometer.

88. The method as set forth in claim 63 wherein the said monitoring is accomplished using a spectrograph with a photodiode array in the focal plane.

89. The method as set forth in claim 63 wherein said introduction of a dopant is made into the plasma gas prior to excitation in the discharge.

90. The method as set forth in claim 63 wherein the dopant introduced is $O_2$.

91. The method as set forth in claim 63 wherein the dopant introduced is a halogen containing compound.

92. The method as set forth in claim 91 wherein the halogen containing compound is $SF_6$.

93. The method of claim 62 comprising the further step of disposing a filter means between said viewing means and said monitoring means for passing red and infrared radiation and absorbing shorter wavelength radiation.

* * * * *